United States Patent
Choi et al.

(10) Patent No.: US 7,510,866 B2
(45) Date of Patent: Mar. 31, 2009

(54) HYBRID BIOREACTOR FOR CELL CULTURE

(75) Inventors: Kuiwon Choi, Seoul (KR); Tae Soo Bae, Seoul (KR); Jung Kyu Kim, Busan (KR); Chang Yang Lee, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 674 days.

(21) Appl. No.: 10/535,141

(22) PCT Filed: Oct. 29, 2003

(86) PCT No.: PCT/KR03/02293

§ 371 (c)(1),
(2), (4) Date: May 17, 2005

(87) PCT Pub. No.: WO2004/046304

PCT Pub. Date: Jun. 3, 2004

(65) Prior Publication Data

US 2006/0068492 A1  Mar. 30, 2006

(30) Foreign Application Priority Data

Nov. 19, 2002  (KR)  .................. 10-2002-0071808

(51) Int. Cl.
*C12M 1/00*  (2006.01)
(52) U.S. Cl. .............. 435/289.1; 435/298.1; 435/298.2; 435/303.2; 435/303.3; 435/379; 623/911; 623/917; 623/924; 73/794; 73/795; 73/796

(58) Field of Classification Search .............. 435/294.1, 435/298.1, 298.2, 303.2, 303.3, 379, 1.2, 435/293.1; 623/911, 917, 924, 926; 73/794, 73/795, 796, 805, 813, 814, 815, 817; 43/61.66

See application file for complete search history.

(56) References Cited

U.S. PATENT DOCUMENTS

| | | | | |
|---|---|---|---|---|
| 3,824,841 | A | * | 7/1974 | Bull .......................... 73/61.66 |
| 4,874,358 | A | * | 10/1989 | Brimhall et al. ............... 494/37 |
| 5,614,089 | A | * | 3/1997 | Allington et al. ......... 210/198.2 |
| 6,048,723 | A | | 4/2000 | Banes |

(Continued)

FOREIGN PATENT DOCUMENTS

JP  10-155475  6/1998

*Primary Examiner*—William H Beisner
*Assistant Examiner*—Michael Hobbs
(74) *Attorney, Agent, or Firm*—Bachman & LaPointe, P.C.

(57) ABSTRACT

A hybrid bioreactor for cell culture is disclosed. To simultaneously apply compressive strain for cell differentiation and shear strain for cell proliferation to cells, the hybrid bioreactor includes a plurality of reactor tube assemblies (100), a compressive strain motor (5), a shear strain motor (25), a lower anchor mount (20) having a plurality of toothed anchors (70) to respectively anchor the lower ends of the reactor tube assemblies (100) to the lower anchor mount (20), a ball screw (90) operated in conjunction with the compressive strain motor (5), an upper anchor mount (60) which engages with the ball screw (90) to vertically move upward and downward and having a plurality of compressive strain anchors (80) to anchor the upper ends of the reactor tube assemblies (100) to the upper anchor mount (60), a power transmission unit to transmit the rotating force of the shear strain motor (25) to the toothed anchors (70).

14 Claims, 7 Drawing Sheets

U.S. PATENT DOCUMENTS 6,057,150 A    5/2000  Lee et al.
6,287,340 B1 * 9/2001  Altman et al. ........... 623/13.11
2002/0098117 A1 * 7/2002  Ammann et al. .............. 422/64

* cited by examiner

Fig. 7

HYBRID BIOREACTOR FOR CELL CULTURE

TECHNICAL FIELD

The present invention relates, in general, to a bioreactor for in vitro culture of animal cells, and, more particularly, to a bioreactor that is capable of applying complex mechanical stimuli, including compressive strain and shear strain, to a reactor tube for culturing animal cells so as to promote the proliferation and differentiation of the cells.

BACKGROUND ART

Tissue engineering is an advanced biotechnology, which cultures animal cells in vitro and applies the cultured animal cells to various fields, including the regeneration of damaged biological tissues, such as the muscular tissues and organs of a human body, the development of artificial organs, and the development of biologically active materials and stimulating agents using protein produced in the cultured animal cells.

The development of the tissue engineering satisfies the increasing demand for proteins used in genetic engineering and used to examine the functions of treatment protein, can be applied to the development of novel medicines, and enables the development of new medical techniques through the development of artificial organs, such as artificial tooth and skin, using animal cell culture techniques, thereby eventually attributing to improvements in social welfare and the quality of life. Behind the development of tissue engineering technology, bioreactors play great roles.

Generally, in accordance with accumulated results through numerous studies of the proliferation and differentiation of animal cells, factors affecting the proliferation and differentiation of animal cells largely fall into three elements playing important roles, which are chemical, electrical and mechanical stimuli.

The studies for applying chemical and electrical stimuli to promote the proliferation and differentiation of animal cells have been actively performed, and this approach has been variously applied to studies in the field of tissue engineering. However, the studies for applying mechanical stimuli to promote the proliferation and differentiation of animal cells have not been actively performed. According to several studies, it has been reported that the differentiation of cells is promoted when compressive strain is applied to the cells, while the proliferation of cells is promoted when shear strain is applied to the cells. Furthermore, there has been introduced a bioreactor that employs only a basic method of applying compressive strain corresponding to a mechanical stimulus to cells simply by adjusting water pressure in a sealed culture vessel.

DISCLOSURE OF THE INVENTION

The present invention has been made in view of conventional techniques, and an object of the present invention is to provide a hybrid bioreactor that is capable of effectively promoting the proliferation and differentiation of animal cells by simultaneously applying to the cells compressive strain and shear strain corresponding to a mechanical stimulus, that is, one of factors promoting the proliferation and differentiation of animal cells.

To achieve the above-described object of the present invention, the present invention provides a hybrid bioreactor for cell culture, including:

a compressive strain motor having a lengthy output shaft;

a main support adapted to contain the compressive strain motor and provided with a hollow support column extending upward;

an upper compressing means including a ball screw for vertical transfer mounted on an upper end of the output shaft of the compressive strain motor, an upper anchor combined with the ball screw and provided with a hollow guide column extending downwardly at a center thereof, and a plurality of compressive strain anchors placed on an outer portion of the upper anchor mount to be rotated on their own axes;

lower anchoring means including a lower anchor mount provided with a through hole at a center thereof and concentrically mounted on the upper support, and a plurality of toothed anchors mounted on an outer portion of the lower anchor mount to be rotated on their own axes;

a shear strain motor around an output shaft of which a main driving gear is fitted;

rotating means including a main rotating shaft fitted into the through hole of the lower anchor mount, a lower shear strain gear located below the lower anchor mount and fitted around the main rotating shaft to be engaged with the main driving gear, and an upper shear strain gear located above the lower anchor mount and fitted around the main rotating shaft to be engaged with all the toothed anchors; and a plurality of reactor tube assemblies installed with upper and lower ends thereof held by the compressive strain anchors and the toothed anchors.

In this case, each of the toothed anchors has a lower small diameter portion mounted on the lower anchor mount through bearings, and an upper large diameter portion toothed on an outer surface thereof and provided with a downwardly extending fitting groove on an upper surface thereof.

Furthermore, each of the compressive strain anchors includes a fitting rod provided with a lower flange part having an upwardly extending fitting groove, a center flange part supporting a spring and an upper flange part preventing from being removed, an upper support block fastened to the upper anchor mount through a bearing and provided with a guide hole to allow the fitting rod to reciprocate through the upper anchor mount, a support housing provided with a through hole at the upper end thereof to allow the fitting rod to pass through the through hole and attached to the upper surface of the upper support block at the lower end brim thereof, and a support spring placed between the center flange part and an upper part of the support housing.

Meanwhile, each of the reactor tube assemblies includes a reactor tube defining a space for culturing cells, a sealing lid sealing an upper opening of the reactor tube and having a compression guide hole at the center thereof, and a compressing rod passing through the compression guide hole and having a compressing head with an outer diameter corresponding to an inner diameter of the reactor tube.

Furthermore, each of the reactor tube assemblies further includes one or more O-rings located between the sealing lid and the compressing rod, and is further provided with a bending prevention member mounted to surround a lower portion of an outside surface of the reactor tube.

Furthermore, the reactor tube is provided with a column-shaped porous cell support therein.

BEST MODE FOR CARRYING OUT THE INVENTION

A preferred embodiment of the present invention is described in detail with reference to the accompanying drawings below.

Figure 1:
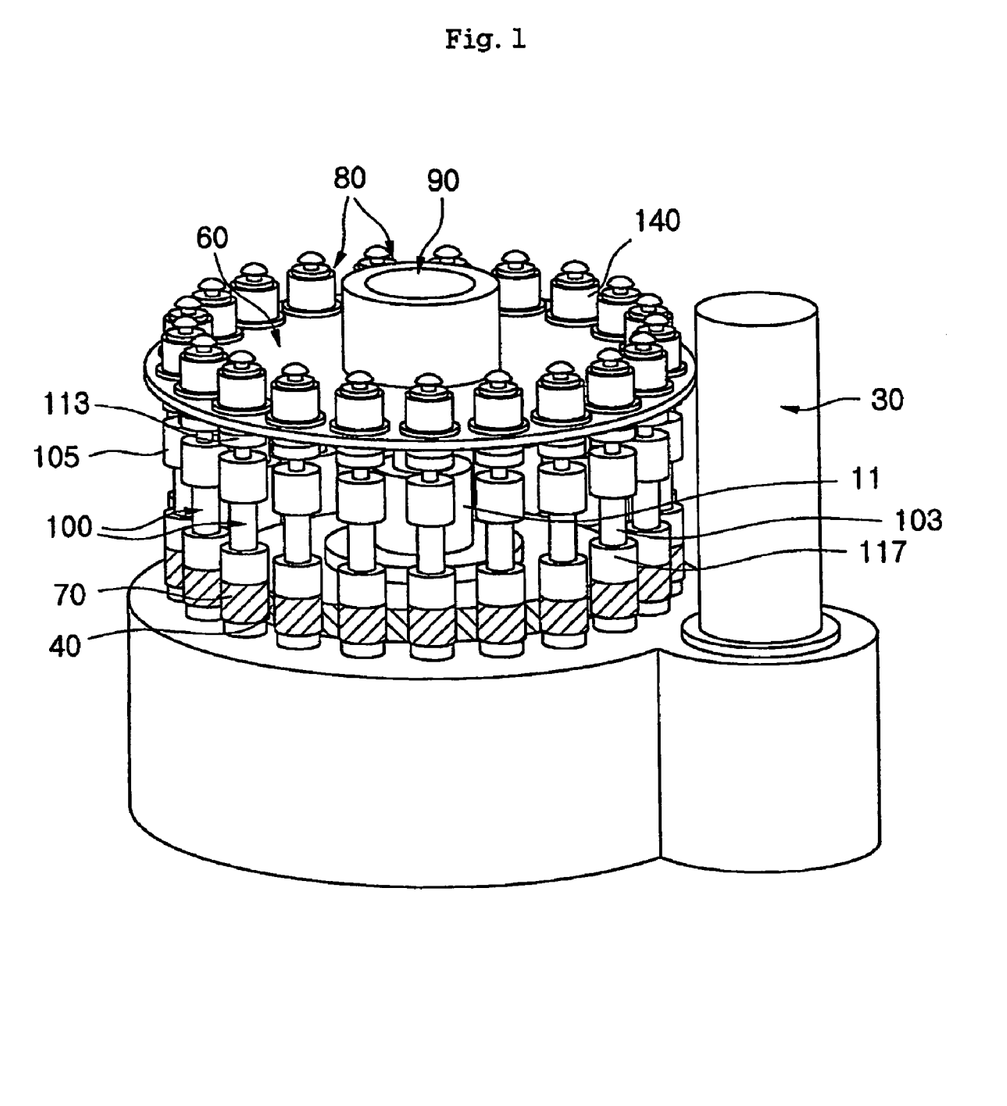
FIG. 1 is a perspective view showing the internal configuration of a bioreactor according to an embodiment of the present invention.
Figure 2:
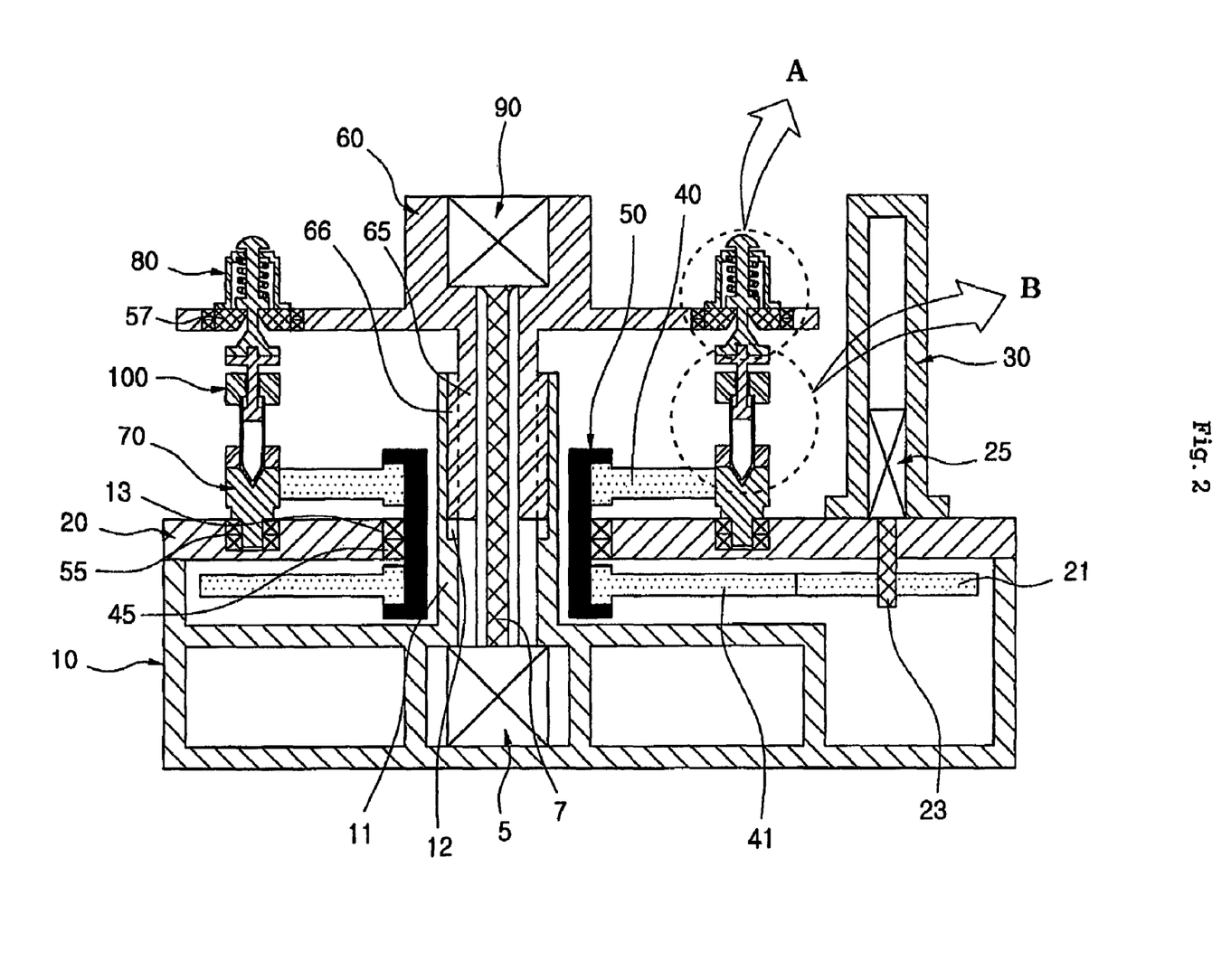
FIG. 2 is a longitudinal section of FIG. 1.

FIG. 1 is a perspective view showing the internal configuration of a hybrid bioreactor according to an embodiment of the present invention, and FIG. 2 is a longitudinal section of FIG. 1.

The hybrid bioreactor according to the preferred embodiment of the present invention includes a compressive strain motor 5, a shear strain motor 25, a main support 10, a lower anchoring means, a rotating means, an upper compressing means, and a plurality of reactor tube assemblies 100.

As shown in FIGS. 1 and 2, the compressive strain motor 5 is contained in the center portion of the main support 10, and the main support 10 is provided with a hollow support column 11 vertically extending above the compressive strain motor 5. The output shaft 7 of the compressive strain motor 5 upwardly passes through the central hollow portion of the support column 11, and is exposed to the outside of the support column 11. Furthermore, a reversible motor must be employed as the compressive strain motor 5.

The lower anchoring means is located above the main support 10, and includes a lower anchor mount 20 attached to the main support 10 and a plurality of toothed anchors 70 mounted on the lower anchor mount 20.

The lower anchor mount 20 is divided into a main support part 18 circularly shaped and a projected part 19 extended from a portion of the circumference of the main support part 18. The main support part 18 is provided with a through hole 13 at the center thereof to receive the main rotating shaft 19, and a plurality of mounting recesses 55 regularly spaced from each other along an imaginary circle near the circumference of the main support 18. The plurality of toothed anchors 70 are mounted into the mounting recesses 55 through bearings 71 to be rotated.

The projected part 19 is provided with a through hole at the center thereof to allow the output shaft 23 of the shear strain motor 25 to pass through the through hole. The shear strain motor 25 is mounted so that the shear strain motor 25 is contained in the motor housing 30 with the output shaft 23 thereof downwardly projected through the through hole formed in the projected part 19. A main driving gear 21 is fitted around the output shaft 23 of the shear strain motor 25 exposed under the projected part 19.

Figure 3:
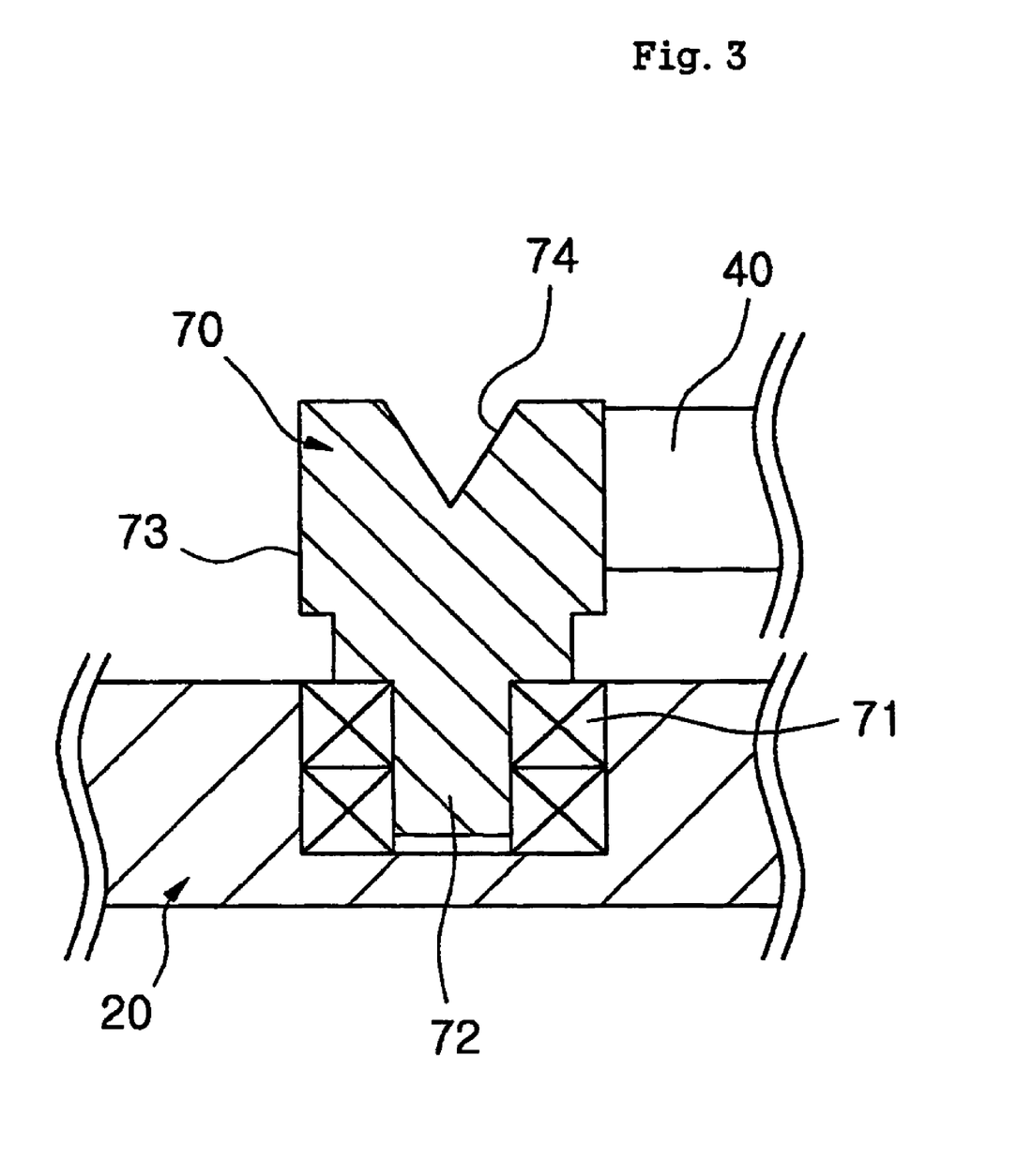
FIG. 3 is a longitudinal section showing the structure of a toothed anchor according to an embodiment of the present invention in detail.

FIG. 3 is a longitudinal section showing the structure of a toothed anchor according to an embodiment of the present invention.

The toothed anchor 70, as shown in FIG. 3, is divided into a small diameter part 72 located in the lower part thereof and a gear part 73 located in the upper part thereof. The small diameter part 72 is held through bearings 71 in the mounting recess 55 of the lower anchor mount 20 to be rotated. The gear part 73 is toothed on the circumferential surface thereof, so that it receives a rotating force in the state of being engaged with an upper shear strain gear 40. The toothed anchor 70 is provided with an engaging recess 74 at the center of the upper surface thereof, and the engaging recess 74 is shaped to correspond to the shape of the lower end of a reactor tube 103.

The rotating means include a main rotating shaft 50, a lower shear strain gear 41, and the upper shear strain gear 40.

As shown in FIG. 2, the main rotating shaft 50 is placed in the through hole of the lower anchor mount 20 through the bearing 45 to be rotated. The lower shear strain gear 41 is fitted around the outside surface of the lower end of the main rotating shaft 50 so that it can be located below the lower anchor mount 20 and be engaged with the main driving gear 21. The upper shear strain gear 40 is fitted around the outside surface of the upper end of the main rotating shaft 50 so that it can be located above the lower anchor mount 20 and be engaged with all the toothed anchors 70.

Accordingly, the rotating force of the shear strain motor 25 is transmitted to the main driving gear 21, the lower shear strain gear 41, the main rotating shaft 50 and the upper shear strain gear 40 in sequence. Finally, the rotating force is transmitted to the toothed anchors 70, thus allowing the toothed anchors 70 to be rotated individually.

For another embodiment of the rotating means, the rotating means may be constructed in such a way that the main driving gear is replaced by a main driving pulley of a smaller diameter to allow the rotating means to be operated in a belt drive manner, the lower shear strain gear is replaced by a lower shear strain pulley, and a belt is provided to allow the two pulleys to be operated in conjunction with each other.

As shown in FIG. 2, an upper compressing means includes a ball screw for vertical transfer 90 mounted on the upper end of the output shaft 7 of the compressive strain motor 5, an upper anchor mount 60 adapted to provide alternating compressing loads to the reactor tube assemblies 100 while being combined with the ball screw 90 and being vertically transferred, and a plurality of compressive strain anchors 80 mounted on the outer portion of the upper anchor mount 60 to hold the upper ends of the plurality of compressive strain anchors 80.

The ball screw 90 is well known. The inside piece of the ball screw 90 whose inside surface is externally threaded is combined with the output shaft 7, and the outside piece of the ball screw 90 internally threaded is combined with the upper anchor mount 60, so that a vertical reciprocating transfer force is transmitted to the reactor tube assemblies 100 through the upper anchor mount 60 to exert alternating compressive loads on the reactor tube assemblies 100.

The upper anchor mount 60, as shown in FIG. 2, is provided with a hollow guide column 65 that is downwardly extended from the center thereof. The guide column 65 is guided by the inside surface of the support column 11 of the main support 10 so that the upper anchor mount 60 can be vertically and smoothly reciprocated while being restrained from being rotated. That is, the support column 11 is provided with a plurality of guide grooves 12 axially formed on the inside surface thereof and the guide column 65 is provided with a plurality of guide rails 66 formed on the outside surface thereof to correspond to the guide grooves 12 so that the relative rotation of the support column 11 and the guide column 65 is restrained and only a vertical, straight reciprocating movement is allowed. Furthermore, the upper anchor mount 60 is provided with a plurality of fitting holes 57 to fit the plurality of compressive strain anchors 80. The fitting holes 57 are regularly arranged along an imaginary circle near the circumference of the main support 18 outside of the radial centerline of the upper anchor mount 60, like the mounting recesses 55, so that the compressive strain anchors 80 vertically correspond to the toothed anchors 70 fitted in the mounting recesses 55 one to one.

Figure 4:
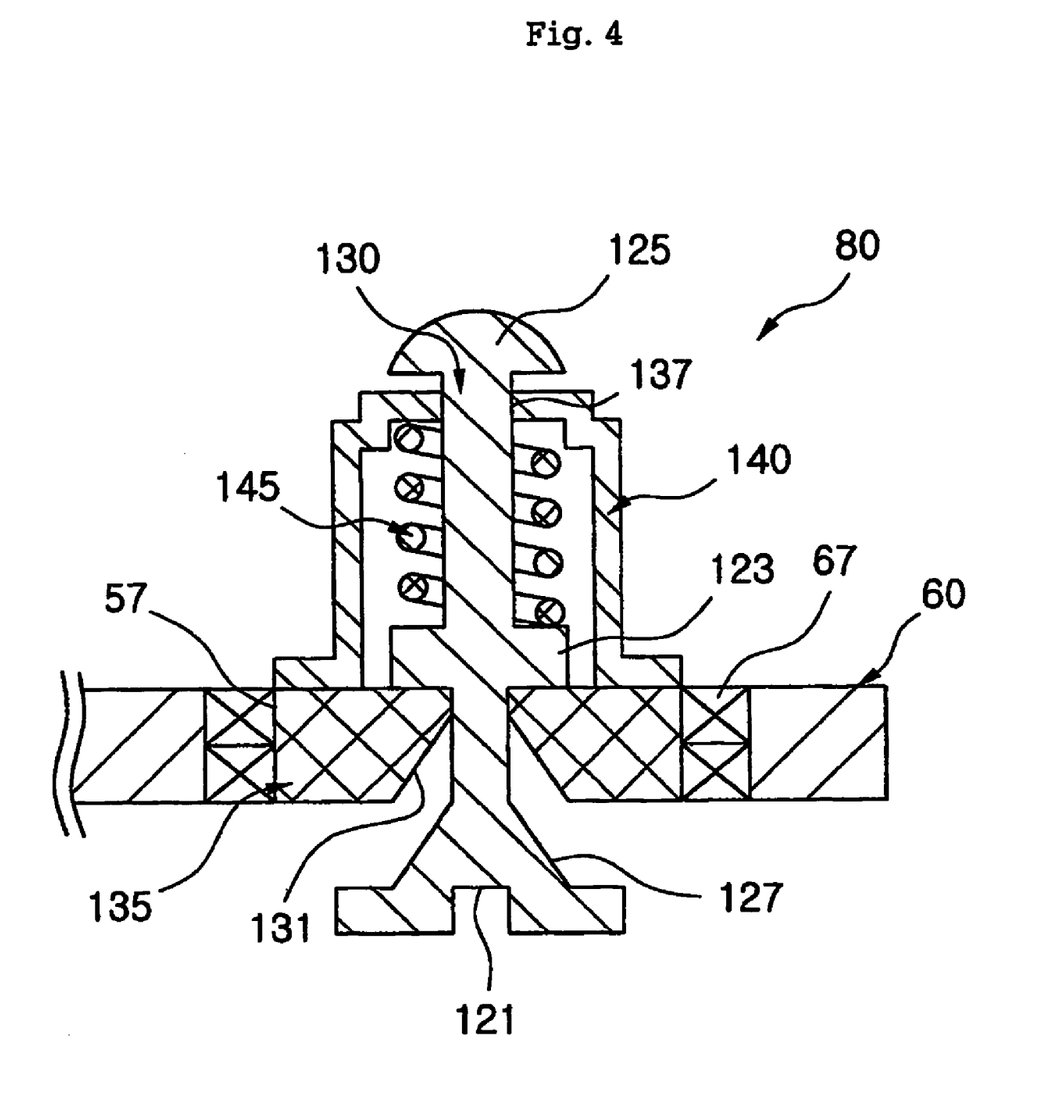
FIG. 4 is a detailed longitudinal section showing a compressive strain anchor according to an embodiment of the present invention, which is shown in portion "A" of FIG. 2.

FIG. 4 is a detailed longitudinal section showing a compressive strain anchor 80 according to an embodiment of the present invention, which is shown in portion "A" of FIG. 2.

The compressive strain anchor 80, as shown in detail in FIG. 4, includes a fitting rod 130 provided with a lower flange part 127 having an upwardly extending fitting groove 121, a center flange part 123 supporting a spring and an upper flange part 125 preventing from being removed, an upper support block 135 fastened to the upper anchor mount 60 through a bearing 67 and provided with a guide hole 131 to allow the fitting rod 130 to reciprocate through the upper anchor mount 60, a support housing 140 provided with a through hole at the upper end thereof to allow the fitting rod 130 to pass through the through hole and attached to the upper surface of the upper support block 135 at the lower end brim thereof, and a support spring 145 placed between the center flange part 123 and the upper part of the support housing 140. Accordingly, it is possible to easily attach and detach the reactor tube assemblies 100, and the reactor tube assemblies 100 can be rotated on their own axes as the toothed anchors 70 are rotated.

The lower flange part 127 of the fitting rod 130 is formed in a taper shape toward the upper end thereof. The guide hole 131 of the upper support block 135 is shaped to correspond to the shape of the lower flange part 127. The fitting rod 130, as shown in FIG. 4, is lowered below the guide hole 131 by the support spring 145, while the fitting rod 130 is rotated while being in contact with the wall of the guide hole 131 as the upper anchor mount 60 is lowered.

Figure 5:
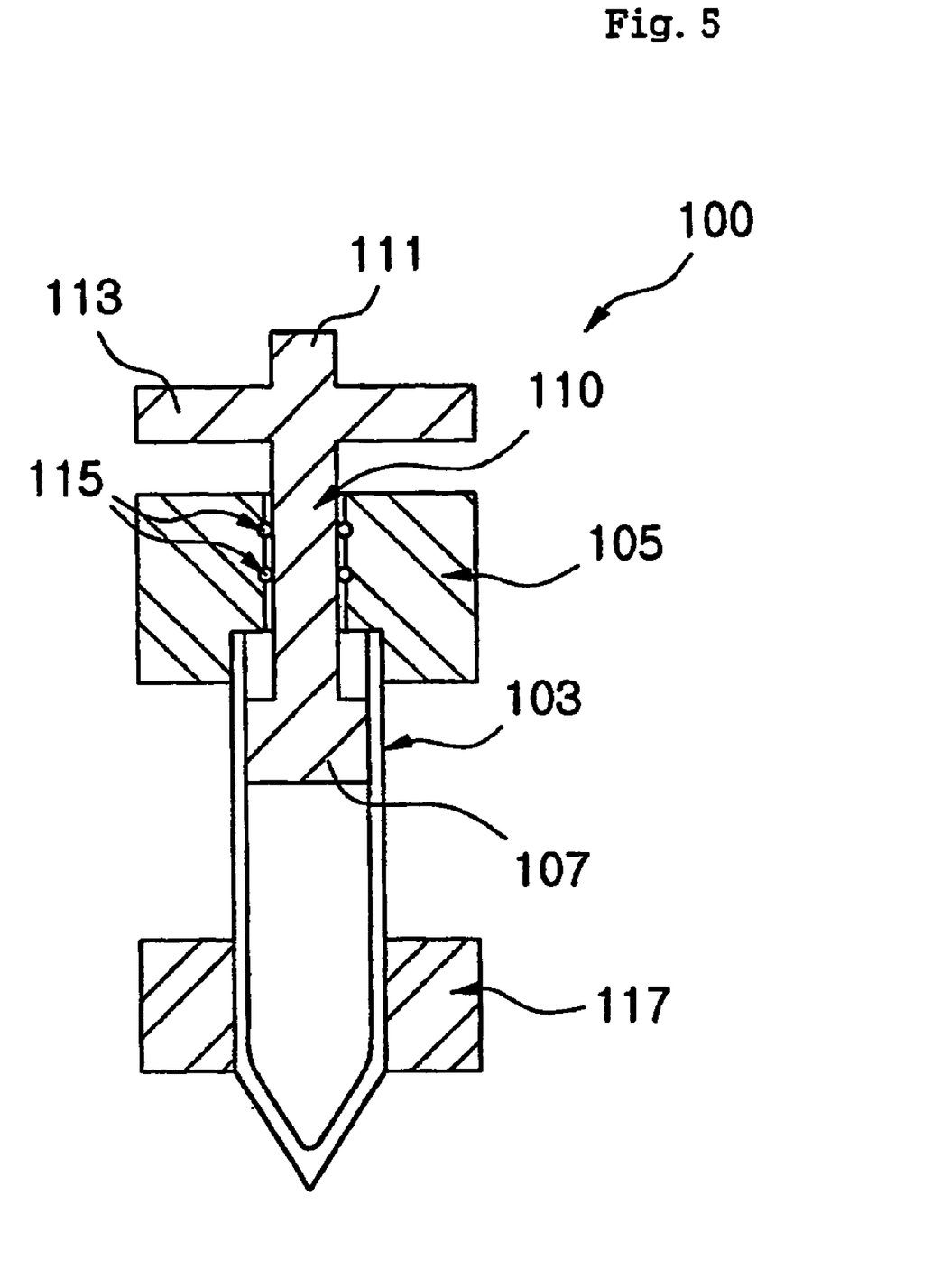
FIG. 5 is a detailed longitudinal section showing a reactor tube assembly according to an embodiment of the present invention, which is shown in portion "B" of FIG. 2.

FIG. 5 is a detailed longitudinal section showing a reactor tube assembly 100 according to an embodiment of the present invention, which is shown in portion "B" of FIG. 2.

Each of the reactor tube assemblies 100 is attached to each of the toothed anchors 70 at the lower end of the reactor tube assembly 100 and to each of the compressive strain anchors 80 at the upper end of the reactor tube assembly 100 so that the reactor tube assembly 100 receives a rotating force transmitted from the rotating means and independently rotates, thus exerting shear strain on cells being cultured in the reactor tube assembly 100.

In more detail, as shown in detail in FIG. 5, the reactor tube assembly 100 includes a reactor tube 103 defining a space for culturing cells, a sealing lid 105 sealing the upper opening of the reactor tube 103 and having a compression guide hole at the center thereof, and a compressing rod 110 passing through the compression guide hole and having a compressing head 107 with an outer diameter corresponding to the inner diameter of the reactor tube 103. Furthermore, the compressing rod 110 is provided with a fitting protrusion 111 and a fitting flange 113 to be securely fitted into the compressive strain anchor 80.

In that case, the sealing lid 105 is provided with one or more O-rings 115, thus completely shutting off the reactor tube 103 from an outside environment.

Meanwhile, the reactor tube 103 is preferably provided with a bending prevention member 117 that is fitted around the lower portion of the outside surface of the reactor tube 103, thus preventing the reactor tube 103 from being bent when a compressing force is exerted on the reactor tube 103.

Figure 6:
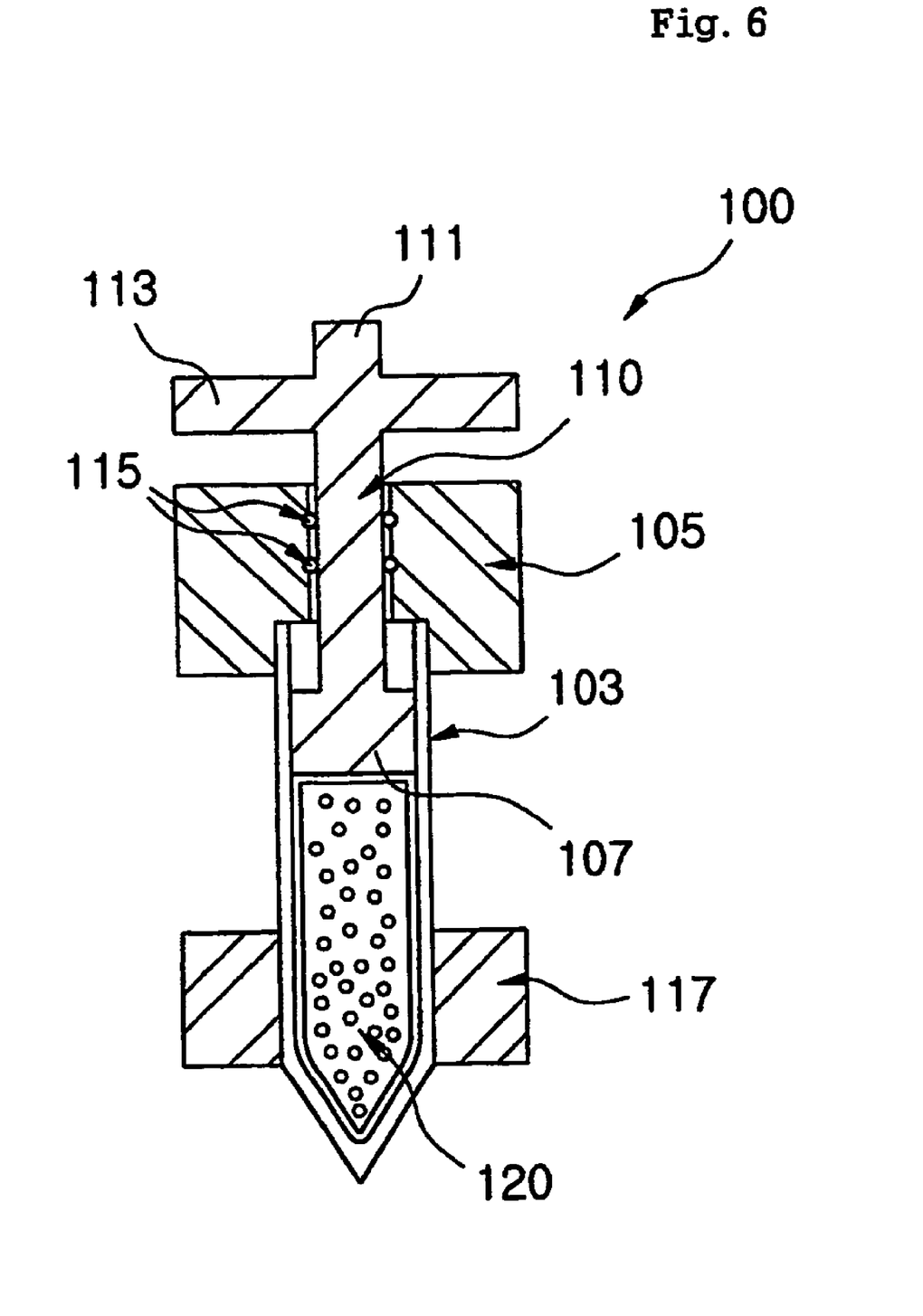
FIG. 6 is a longitudinal section showing a reactor tube assembly according another embodiment of the present invention in detail.

FIG. 6 is a longitudinal section showing a reactor tube assembly according another embodiment of the present invention in detail.

The reactor tube 103, as shown in FIG. 6, may be provided with a column-shaped porous cell support 120 having a volume and a shape corresponding to those of the inner space of the reactor tube 103 to provide a sufficient surface area when adherent animal cells are cultured in the reactor tube 103.

The porous cell support 120 is fabricated using a natural polymer or a synthetic polymer, for example, a natural polymer such as chitosan or collagen, or a synthetic polymer such as PLGA, PLA or PLLA. The porous cell support 120, which is used to maximize the area to which animal cells attach, has a pore size of about 150 to 400 µm.

The hybrid bioreactor can be used to promote the proliferation and differentiation of both suspension cells and adherent cells simply by changing the reactor tube assemblies 100 without change of other elements.

Figure 7:
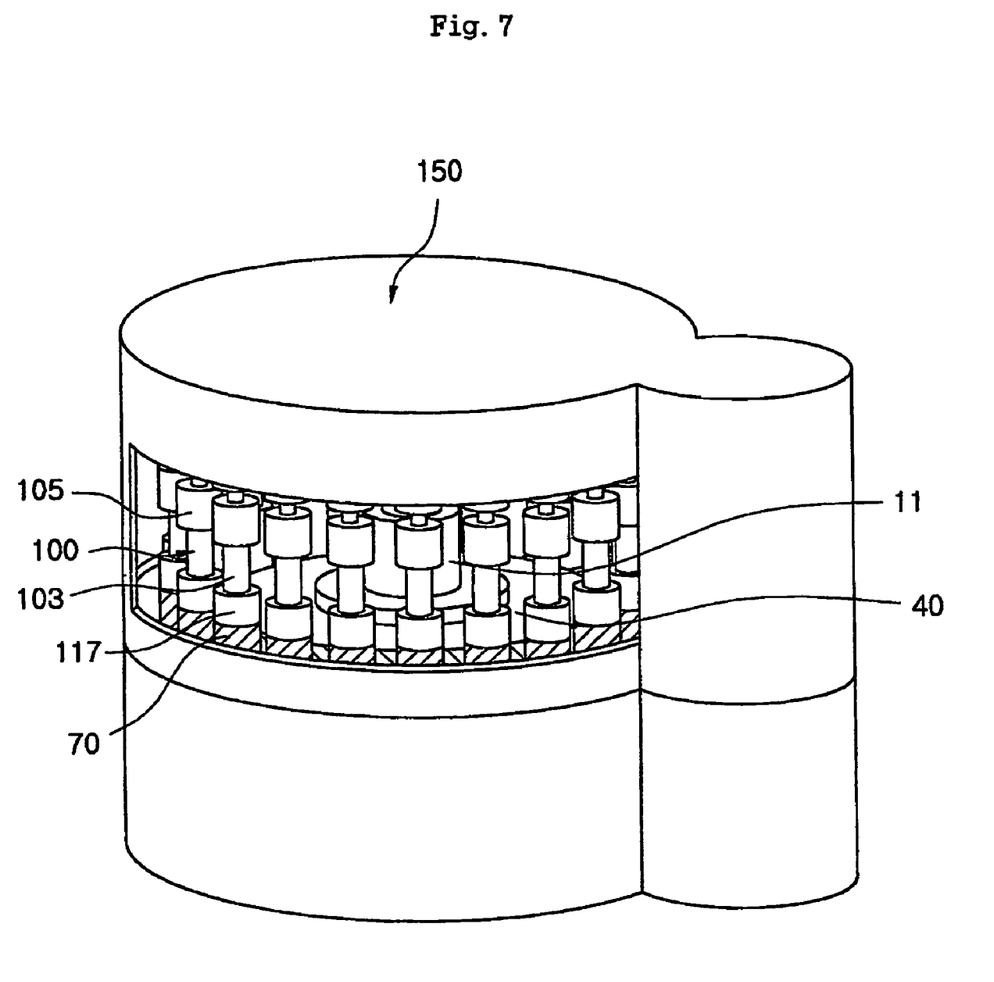
FIG. 7 is a perspective view of the bioreactor of the present invention with an outer casing worn thereon.

FIG. 7 is a perspective view of the bioreactor of the present invention with an outer casing 150 worn thereon.

The bioreactor according to the present invention described above, as shown in FIG. 7, is used to promote the proliferation and differentiation of animal cells with the outer casing 150 worn thereon, independently or in an incubator.

The operations of the hybrid bioreactor according to the present invention are described below.

First, the reactor tube assembles 100, in which cells to be cultured are contained, are each placed between one toothed anchor 70 and one compressive strain anchor 80. The reactor tube assembly 100 is mounted to be elastically supported by the support spring 145 in such a way that the lower end of the reactor tube assembly 100, that is, the lower end of the reactor tube 103, is inserted into the engaging recess 74 of the toothed anchor 70 fitted into the mounting recess 55, the fitting rod 130 of the translation strain anchor 80 is raised against the force of the support spring 145, and a force used to raise the fitting rod 130 is released after the fitting protrusion 111 is inserted into the fitting groove 121 of the fitting rod 130.

In that state, operations of providing compressive strain and shear strain to the reactor tubes 100 start. Prior to main operations, the compressive strain motor 5 rotates at a certain angle to lower the upper anchor mount 60, thus bringing the lower flange part 127 of the fitting rod 130 having an inclined outer surface into tight contact with the guide hole 131 of the upper support block 135. From this state, the main operations start.

As the shear strain motor 25 mounted in the motor housing 30 is rotated, the lower shear strain gear 41 of the rotating means engaged with the main driving gear 21 fitted around the output shaft 23 of the shear strain motor 25 is rotated. As the lower shear strain gear 41 is rotated, the main rotating shaft 50 and the upper shear strain gear 40 fitted around the main rotating shaft 50 are rotated. Accordingly, all the toothed anchors 70 engaged with the upper shear strain gear 40 are rotated on their own axes.

The main driving gear 21 and the lower shear strain gear 41 are preferably formed to have a rotational ratio of 7:1 or 8:1. Shear strain is allowed to be exerted on cells being cultured in the reactor tube assemblies 100 while the rotational speed of the reactor tube assemblies 100 has been adjusted to 1000 rpm or less according to the kind of cells being cultured.

The compressive strain motor 5 is controlled to repeat forward and reverse rotations at a speed of 0.5 to 1.0 Hz, so that alternating compressive loads caused by the ball screw 90 and the upper anchor mount 60 are transmitted to the reactor tube assemblies 100 and compressive strain is exerted on the cells being cultured in the reactor tube assemblies 100. In this case, the maximum compressive load exerted is controlled to the extent to which a maximum compressive strain of 10% can be implemented.

The cell culturing operations described above is performed so that alternating compressive loads are applied to the reactor tube assemblies 100 at a maximum of $10^6$ cycles per process, and the number of repetitions can be appropriately adjusted according to the kind of cells and the purpose of culturing cells.

INDUSTRIAL APPLICABILITY

The hybrid bioreactor according to the present invention as described above is capable of simultaneously applying compressive strain, which promotes the proliferation of cells, and shear strain, which promotes the differentiation of cells, so that it has the effect of simultaneously promoting the proliferation and differentiation of cells being cultivated while being contained in the reactor tube assemblies in a mechanical manner.

Furthermore, in the case where the culture tube is provided with the porous cell support, it is possible to culture adherent cells. In the case where the culture tube is not provided with the porous cell support, it is possible to culture suspension cells. For example, the hybrid bioreactor of the present invention may be used to promote the proliferation and differentiation of various animal cells, including bone cells, chondrocytes, osteosarcoma cell line, fibroblasts, stromal cells and mesenchymal stem cells. Therefore, the hybrid bioreactor of the present invention can contribute greatly to tissue engineering research that has been developed and becomes important recently.

Furthermore, if moisture-proof motors are employed as the motors of the bioreactor, the bioreactor have various uses, such as use within an incubator.

Although the present invention has been described in conjunction with the specific embodiments, those skilled in the art can easily appreciate that various modifications and changes are possible without departing from the scope and spirit of the invention as disclosed in the accompanying claims.

The invention claimed is:

1. A hybrid bioreactor for cell culture, comprising:
   a plurality of reactor tube assemblies;
   a compressive strain motor;
   a ball screw coupled to be operated in conjunction with the compressive strain motor;
   an upper anchor mount vertically reciprocated while being combined with the ball screw and provided with a plurality of compressive strain anchors holding lower ends of the reactor tube assemblies, wherein each of the compressive strain anchors comprises a fitting rod provided with a lower flange part having an upwardly extending fitting groove, a center flange part supporting a spring and an upper flange part preventing from being removed, an upper support block fastened to the upper anchor mount through a bearing and provided with a guide hole to allow the fitting rod to reciprocate through the upper anchor mount, a support housing provided with a through hole at the upper end thereof to allow the fitting rod to pass through the through hole and attached to the upper surface of the upper support block at the lower end brim thereof, and a support spring placed between the center flange part and an upper part of the support housing;
   a lower anchor mount adapted to hold lower ends of the reactor tube assemblies and provided with a plurality of toothed anchors on outer surface of which teeth are formed;
   a shear strain motor; and
   power transmitting means for transmitting a rotating force of the shear strain motor to the plurality of toothed anchors.

2. The hybrid bioreactor as set forth in claim 1, wherein the power transmitting means comprises:
   a main driving gear fitted around an output shaft of the shear strain motor;
   a hollow main rotating shaft placed in a center portion of the lower anchor mount to be rotated;
   a lower shear strain gear located below the lower anchor mount and fitted around the main rotating shaft to be engaged with the main driving gear; and
   an upper shear strain gear located above the lower anchor mount and fitted around the main rotating shaft to be engaged with the main drive shaft.

3. The hybrid bioreactor as set forth in claim 1, wherein the power transmitting means comprises:
   a main drive pulley fitted around an output shaft of the shear strain motor;
   a hollow main rotating shaft placed in a center portion of the lower anchor mount to be rotated;
   a lower shear strain pulley fitted around the main drive shaft to be located below the lower anchor mount and coupled to the main drive pulley with a belt; and
   an upper shear strain gear located above the lower anchor mount and fitted around the main rotating shaft to be engaged with all the toothed anchors.

4. The hybrid bioreactor as set forth in claim 1, wherein each of the toothed anchors has a lower small diameter portion mounted on the lower anchor mount through bearings, and an upper large diameter portion toothed on an outer surface thereof and provided with a downwardly extending fitting groove on an upper surface thereof.

5. The hybrid bioreactor as set forth in claim 1, each of the reactor tube assemblies comprises a reactor tube defining a space for culturing cells, a sealing lid sealing an upper opening of the reactor tube and having a compression guide hole at the center thereof, and a compressing rod passing through the compression guide hole and having a compressing head with an outer diameter corresponding to an inner diameter of the reactor tube.

6. The hybrid bioreactor as set forth in claim 5, wherein each of the reactor tube assemblies further comprises one or more O-rings located between the sealing lid and the compressing rod.

7. The hybrid bioreactor as set forth in claim 6, wherein each of the reactor tube assemblies is further provided with a bending prevention member mounted to surround a lower portion of an outside surface of the reactor tube.

8. The hybrid bioreactor as set forth in claim 7, wherein the reactor tube is provided with a column-shaped porous cell support therein.

9. A hybrid bioreactor for cell culture, comprising:
   a compressive strain motor having a lengthy output shaft;
   a main support adapted to contain the compressive strain motor and provided with a hollow support column extending upward;
   an upper compressing means comprising a ball screw for vertical transfer mounted on an upper end of the output shaft of the compressive strain motor, an upper anchor combined with the ball screw and provided with a hollow guide column extending downwardly at a center thereof, and a plurality of compressive strain anchors placed on an outer portion of the upper anchor mount to be rotated on their own axes, wherein each of the compressive strain anchors comprises a fitting rod provided with a lower flange part having an upwardly extending fitting groove, a center flange part supporting a spring and an upper flange part preventing from being removed, an upper support block fastened to the upper anchor mount through a bearing and provided with a guide hole to allow the fitting rod to reciprocate through the upper anchor mount, a support housing provided with a through hole at the upper end thereof to allow the fitting rod to pass through the through hole and attached to the upper surface of the upper support block at the lower end brim thereof, and a support spring placed between the center flange part and an upper part of the support housing;

lower anchoring means comprising a lower anchor mount provided with a through hole at a center thereof and concentrically mounted on the upper support, and a plurality of toothed anchors mounted on an outer portion of the lower anchor mount to be rotated on their own axes;

a shear strain motor around an output shaft of which a main driving gear is fitted;

rotating means comprising a main rotating shaft fitted into the through hole of the lower anchor mount, a lower shear strain gear located below the lower anchor mount and fitted around the main rotating shaft to be engaged with the main driving gear, and an upper shear strain gear located above the lower anchor mount and fitted around the main rotating shaft to be engaged with all the toothed anchors; and a plurality of reactor tube assemblies installed with upper and lower ends thereof held by the compressive strain anchors and the toothed anchors.

10. The hybrid bioreactor as set forth in claim 9, wherein each of the toothed anchors has a lower small diameter portion mounted on the lower anchor mount through bearings, and an upper large diameter portion toothed on an outer surface thereof and provided with a downwardly extending fitting groove on an upper surface thereof.

11. The hybrid bioreactor as set forth in claim 9, each of the reactor tube assemblies comprises a reactor tube defining a space for culturing cells, a sealing lid sealing an upper opening of the reactor tube and having a compression guide hole at the center thereof, and a compressing rod passing through the compression guide hole and having a compressing head with an outer diameter corresponding to an inner diameter of the reactor tube.

12. The hybrid bioreactor as set forth in claim 11, wherein each of the reactor tube assemblies further comprises one or more O-rings located between the sealing lid and the compressing rod.

13. The hybrid bioreactor as set forth in claim 12, wherein each of the reactor tube assemblies is further provided with a bending prevention member mounted to surround a lower portion of an outside surface of the reactor tube.

14. The hybrid bioreactor as set forth in claim 13, wherein the reactor tube is provided with a column-shaped porous cell support therein.

* * * * *